US007888502B2

(12) United States Patent
Wu

(10) Patent No.: US 7,888,502 B2
(45) Date of Patent: Feb. 15, 2011

(54) TITANYL PHTHALOCYANINE PROCESSES AND PHOTOCONDUCTORS THEREOF

(75) Inventor: Jin Wu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 902 days.

(21) Appl. No.: 11/769,067

(22) Filed: Jun. 27, 2007

(65) Prior Publication Data

US 2009/0005555 A1 Jan. 1, 2009

(51) Int. Cl.
*C07B 42/00* (2006.01)
*C07D 487/22* (2006.01)

(52) U.S. Cl. .................................................... 540/145

(58) Field of Classification Search .................. 540/145
See application file for complete search history.

(56) References Cited

U.S. PATENT DOCUMENTS

| | | | |
|---|---|---|---|
| 3,121,006 | A | 2/1964 | Middleton et al. |
| 4,265,990 | A | 5/1981 | Stolka et al. |
| 4,298,697 | A | 11/1981 | Baczek |
| 4,338,390 | A | 7/1982 | Lu |
| 4,560,635 | A | 12/1985 | Hoffend et al. |
| 5,153,094 | A | 10/1992 | Kazmaier et al. |
| 5,166,339 | A | 11/1992 | Duff et al. |
| 5,189,155 | A | 2/1993 | Mayo et al. |
| 5,189,156 | A | 2/1993 | Mayo et al. |
| 5,473,064 | A | 12/1995 | Mayo et al. |
| 5,482,811 | A | 1/1996 | Keoshkerian et al. |
| 5,521,306 | A | 5/1996 | Burt et al. |
| 5,703,487 | A | 12/1997 | Mishra |
| 6,008,653 | A | 12/1999 | Popovic et al. |
| 6,150,824 | A | 11/2000 | Mishra et al. |
| 6,376,141 | B1 | 4/2002 | Mishra et al. |
| 6,544,701 | B2 | 4/2003 | Tadokoro et al. |
| 6,713,220 | B2 | 3/2004 | Graham et al. |
| 6,913,863 | B2 | 7/2005 | Wu et al. |
| 7,033,715 | B2 | 4/2006 | Molaire |
| 2006/0105254 | A1 | 5/2006 | Wu et al. |

OTHER PUBLICATIONS

U.S. Application No., filed concurrently herewith, on Hydroxygallium Phthalocyanine Processes and Photoconductors Thereof.
U.S. Appl. No. 11/602,033, filed Nov. 20, 2006 on Titanyl Phthalocyanine Photoconductors.
U.S. Appl. No. 11/472,765, filed Jun. 22, 2006 on Titanyl Phthalocyanine Photoconductors.
U.S. Appl. No. 11/472,766, filed Jun. 22, 2006 on Titanyl Phthalocyanine Photoconductors.
U.S. Appl. No. 11/458,467, filed Jul. 19, 2006 on Electrophotographic Photoreceptor.

*Primary Examiner*—Paul V. Ward
(74) *Attorney, Agent, or Firm*—Oliff & Berridge, PLC

(57) ABSTRACT

A process which includes treating, mixing, or contacting a Type I titanyl phthalocyanine with a weak acid with a pKa of at least equal to or greater than about 0; dissolving the acid treated Type I titanyl phthalocyanine in a solution of a trihaloacetic acid and an alkylene halide; adding the formed mixture to a solution of an alcohol and an alkylene halide thereby precipitating a Type Y titanyl phthalocyanine; and treating the Type Y titanyl phthalocyanine with monohalobenzene thereby resulting in a high sensitivity titanyl phthalocyanine.

17 Claims, No Drawings

TITANYL PHTHALOCYANINE PROCESSES AND PHOTOCONDUCTORS THEREOF

CROSS REFERENCE TO RELATED APPLICATIONS

In U.S. application Ser. No. (11/769,073), filed concurrently herewith, on Hydroxygallium Phthalocyanine Processes and Photoconductors Thereof, there is illustrated a process which comprises treating a hydroxygallium phthalocyanine Type I with a weak acid having a pKa of at least equal to or greater than about −3, and subsequently contacting said hydroxygallium phthalocyanine Type I with an organic solvent.

In U.S. application Ser. No. 11/602,033 filed Nov. 20, 2006 on Titanyl Phthalocyanine Photoconductors, the disclosure of which is totally incorporated herein by reference, there is illustrated a photoconductor comprising an optional supporting substrate, a photogenerating layer, and at least one charge transport layer comprised of at least one charge transport component, and wherein the photogenerating layer contains a titanyl phthalocyanine prepared by dissolving a Type I titanyl phthalocyanine in a solution comprising a trihaloacetic acid and an alkylene halide; adding the resulting mixture comprising the dissolved Type I titanyl phthalocyanine to a solution comprising an alcohol and an alkylene halide thereby precipitating a Type Y titanyl phthalocyanine; and treating the Type Y titanyl phthalocyanine with a monohalobenzene, and wherein the photogenerating layer is prepared from a dispersion of said titanyl phthalocyanine, a polymer binder, and a chlorinated solvent of at least one of dichloroethane and dichloropropane U.S. application Ser. No. 11/472,765 and Ser. No. 11/472,766, both filed Jun. 22, 2006, relating to titanyl phthalocyanine photoconductors, the disclosures of which are totally incorporated herein by reference, and wherein there is illustrated, for example, a photoconductor wherein the photogenerating layer contains a titanyl phthalocyanine prepared by dissolving a Type I titanyl phthalocyanine in a solution comprising a trihaloacetic acid and an alkylene halide; adding the mixture comprising the dissolved Type I titanyl phthalocyanine to a solution comprising an alcohol and an alkylene halide thereby precipitating a Type Y titanyl phthalocyanine; and treating the Type Y titanyl phthalocyanine with a monohalobenzene.

U.S. application Ser. No. 11/458,467, filed Jul. 19, 2006, the disclosure of which is totally incorporated herein by reference, and wherein there is illustrated, for example, a photoconductor wherein the photogenerating layer contains a titanyl phthalocyanine, a film-forming polymer binder; and a glycol compound having two hydroxyl groups bonded to adjoining carbon atoms in the carbon chain.

U.S. application Ser. No. 10/992,500, U.S. Publication No. 20060105254,filed Nov. 18, 2004, the disclosure of which is totally incorporated herein by reference, and wherein there is illustrated, for example, a process for the preparation of a Type V titanyl phthalocyanine, the process comprising providing a Type I titanyl phthalocyanine; dissolving the Type I titanyl phthalocyanine in a solution comprising a trihaloacetic acid and an alkylene halide; adding the resulting mixture comprising the dissolved Type I titanyl phthalocyanine to a solution comprising an alcohol and an alkylene halide thereby precipitating a Type Y titanyl phthalocyanine; and treating the Type Y titanyl phthalocyanine with monochlorobenzene.

A number of the components of the above cross referenced applications, such as the supporting substrates, resin binders, antioxidants, charge transport components, hole blocking layer components, adhesive layers, titanyl phthalocyanine preparation components and reaction conditions, and the like, may be selected for the photoconductor and imaging members of the present disclosure in embodiments thereof.

BACKGROUND

This disclosure is generally directed to processes for the preparation of titanyl phthalocyanines, especially a highly photosensitive titanyl phthalocyanines like titanyl phthalocyanine Type V, and drum and belt layered photoreceptors, photoconductors thereof, and the like. More specifically, the present disclosure is directed to titanyl phthalocyanine processes where weak acids are selected, and to multilayered flexible or belt imaging members or devices comprised of an optional supporting medium like a substrate, a photogenerating layer containing the prepared titanyl phthalocyanine, and a charge transport layer, including a plurality of charge transports layers, such as a first charge transport layer and a second charge transport layer, an optional adhesive layer, an optional hole blocking or undercoat layer, an optional overcoating layer, and wherein at least one of the charge transport layers contains at least one charge transport component, a polymer or resin binder, and an optional antioxidant.

More specifically, there is illustrated herein in embodiments the incorporation into imaging members of suitable high photosensitivity photogenerating pigments, such as certain titanyl phthalocyanines, which photosensitivity is, for example, from about 10 to about 50 percent higher than that of a similar photoconductor containing as a photogenerating pigment hydroxygallium phthalocyanine Type V; a hole transport layer thereover, and which layer permits the rapid transport of holes, and wherein the photogenerating dispersion is comprised of a photogenerating pigment or pigments of titanyl phthalocyanine prepared as illustrated herein, an optional polymer binder and a chlorinated solvent, such as dichlorinated solvents or monochlorobenzene, which dispersion or mixture is deposited on the photoconductor substrate or other photoconductor layers. The selection of certain halogenated, such as chlorinated, solvents together with using weak acids in the washing of a titanyl phthalocyanine intermediate provides, for example, for the capture of impurities, such as titanium oxide, titanium chloride, or other organic titanates, and thereby generates a high sensitivity titanyl phthalocyanine with lower CDS characteristics than when a weak acid is not used. High dispersion stability and improved potlife are particularly desirable from the manufacturing point of view as the dispersion can be used over an extended period of time, like several days, without a negative impact on the coating process and the photosensitivity of the coated photoreceptors. Poor dispersion stability can result in the pigment settling out quickly to prevent or inhibit a uniform coating of the photogenerating layer. When the photosensitivity of coated photoconductor does not substantially change with the aging of the titanyl phthalocyanine dispersion, then the useful life of the dispersion (potlife) is prolonged allowing efficient utilization of the dispersion materials with minimum waste. Also, the excellent photosensitivity characteristics of the titanyl phthalocyanine obtained can be maintained for suitable periods of time.

Additionally, in embodiments the photoconductors disclosed herein permit minimal undesirable CDS developed image characteristics, excellent and in a number of instances low $V_r$ (residual potential), and allow the substantial prevention of $V_r$ cycle up when appropriate; high stable sensitivity; low acceptable image ghosting characteristics; and desirable toner cleanability.

Also included within the scope of the present disclosure are methods of imaging and printing with the photoconductor devices illustrated herein. These methods generally involve the formation of an electrostatic latent image on the imaging member, followed by developing the image with a toner composition comprised, for example, of thermoplastic resin, colorant, such as pigment, charge additive, and surface additives, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same operation with the exception that exposure can be accomplished with a laser device or image bar. More specifically, the imaging members and flexible belts disclosed herein can be selected for the Xerox Corporation iGEN3® machines that generate with some versions over 100 copies per minute. Processes of imaging, especially xerographic imaging and printing, including digital, and/or color printing are thus encompassed by the present disclosure.

The photoconductors disclosed herein are in embodiments sensitive in the wavelength region of, for example, from about 400 to about 900 nanometers, and in particular from about 650 to about 850 nanometers, thus diode lasers can be selected as the light source. Moreover, the imaging members disclosed herein are in embodiments useful in high resolution color xerographic applications, particularly high-speed color copying and printing processes.

REFERENCES

Disclosed in U.S. Pat. No. 7,033,715 is a process for the formation of a nanoparticulate crystalline titanium phthalocyanine pigments, which can be selected as a photogenerating pigment by contacting the pigment with substantially pure 1,1,2-trichloroethane (TCE) under conditions so as to convert the titanium phthalocyanine pigment to a nanoparticulate crystalline composition.

A number of titanyl phthalocyanines, oxytitanium phthalocyanines, or photogenerating pigments are known to absorb near infrared light around 800 nanometers, and may exhibit improved sensitivity compared to other pigments, such as, for example, hydroxygallium phthalocyanine. Generally, titanyl phthalocyanine is known to have five main crystal forms known as Types I, II, III, X, and IV. For example, U.S. Pat. Nos. 5,189,155 and 5,189,156, the entire disclosures of which are incorporated herein by reference, disclose a number of methods for obtaining various polymorphs of titanyl phthalocyanine. Additionally, U.S. Pat. Nos. 5,189,155 and 5,189,156 are directed to processes for obtaining Types I, X, and IV phthalocyanines. U.S. Pat. No. 5,153,094, the entire disclosure of which is incorporated herein by reference, relates to the preparation of titanyl phthalocyanine polymorphs including Types I, II, III, and IV polymorphs. U.S. Pat. No. 5,166,339, the disclosure of which is totally incorporated herein by reference, discloses processes for preparing Types I, IV, and X titanyl phthalocyanine polymorphs, as well as the preparation of two polymorphs designated as Type Z-1 and Type Z-2.

There is illustrated in U.S. Pat. No. 6,913,863, the disclosure of which is totally incorporated herein by reference, a photoconductive imaging member comprised of a hole blocking layer, a photogenerating layer, and a charge transport layer, and wherein the hole blocking layer is comprised of a metal oxide; and a mixture of a phenolic compound and a phenolic resin wherein the phenolic compound contains at least two phenolic groups.

Layered photoconductors have been described in numerous U.S. patents, such as U.S. Pat. No. 4,265,990, the disclosure of which is totally incorporated herein by reference. Examples of photogenerating layer components disclosed in U.S. Pat. No. 4,265,990 include trigonal selenium, metal phthalocyanines, vanadyl phthalocyanines, and metal free phthalocyanines. Additionally, there is described in U.S. Pat. No. 3,121,006, the disclosure of which is totally incorporated herein by reference, a photoconductive member comprised of finely divided particles of a photoconductive inorganic compound dispersed in an electrically insulating organic resin binder.

In U.S. Pat. No. 6,544,701 there is disclosed a process for the preparation of photogenerating pigments, such as a oxytitanium phthalocyanine, by reacting a nitrile derivative, a phthalonitrile or a 1,3-diiminoisoindoline derivative, and as necessary a metal or metal containing compound.

There is illustrated in U.S. Pat. No. 5,521,306, the disclosure of which is totally incorporated herein by reference, a process for the preparation of Type V hydroxygallium phthalocyanine comprising the in situ formation of an alkoxy-bridged gallium phthalocyanine dimer, hydrolyzing the dimer to hydroxygallium phthalocyanine, and subsequently converting the hydroxygallium phthalocyanine product to Type V hydroxygallium phthalocyanine.

Illustrated in U.S. Pat. No. 5,482,811, the disclosure of which is totally incorporated herein by reference, is a process for the preparation of hydroxygallium phthalocyanine photogenerating pigments which comprises hydrolyzing a gallium phthalocyanine precursor pigment by dissolving the hydroxygallium phthalocyanine in a strong acid, and then reprecipitating the resulting dissolved pigment in basic aqueous media; removing any ionic species formed by washing with water, concentrating the resulting aqueous slurry comprised of water and hydroxygallium phthalocyanine to a wet cake; removing water from said slurry by azeotropic distillation with an organic solvent, and subjecting said resulting pigment slurry to mixing with the addition of a second solvent to cause the formation of said hydroxygallium phthalocyanine polymorphs.

Also, in U.S. Pat. No. 5,473,064, the disclosure of which is totally incorporated herein by reference, there is illustrated a process for the preparation of photogenerating pigments of hydroxygallium phthalocyanine Type V essentially free of chlorine, whereby a pigment precursor Type I chlorogallium phthalocyanine is prepared by reaction of gallium chloride in a solvent, such as N-methylpyrrolidone, present in an amount of from about 10 parts to about 100 parts, and more specifically, about 19 parts with 1,3-diiminoisoindolene ($DI^3$) in an amount of from about 1 part to about 10 parts, and more specifically, about 4 parts of $DI^3$, for each part of gallium chloride that is reacted; hydrolyzing said pigment precursor chlorogallium phthalocyanine Type I by standard methods, for example acid pasting, whereby the pigment precursor is dissolved in concentrated sulfuric acid and then reprecipitated in a solvent, such as water, or a dilute ammonia solution, for example from about 10 to about 15 percent; and subsequently treating the resulting hydrolyzed pigment hydroxygallium phthalocyanine Type I with a solvent, such as N,N-dimethylformamide, present in an amount of from about 1 volume part to about 50 volume parts, and preferably about 15 volume parts for each weight part of pigment hydroxygallium phthalocyanine that is used by, for example, ball milling the Type I hydroxygallium phthalocyanine pigment in the presence of spherical glass beads, approximately 1 millimeter to 5 millimeters in diameter, at room temperature, about 25° C., for a period of from about 12 hours to about 1 week, and preferably about 24 hours.

The process for the preparation of photoconductors using dispersions is susceptible to many variables, such as, for example, material variables, including contents and purity of the material; the photogenerating dispersion components selected and amounts thereof; process variables, including milling time and milling procedure; and coating process variables, including web coating, dip coating, the drying process of several layers, the time interval between the coatings of successive layers, and the like. The net outcome of these variables is, for example, that the electrical characteristics of the prepared photoreceptors may be inconsistent during the manufacturing process.

Sensitivity is a valuable electrical characteristic of electrophotographic imaging members or photoreceptors. Sensitivity may be described in two aspects. The first aspect of sensitivity is spectral sensitivity, which refers to sensitivity as a function of wavelength. An increase in spectral sensitivity implies an appearance of sensitivity at a wavelength in which previously no sensitivity was detected. The second aspect of sensitivity, broadband sensitivity, is a change of sensitivity, for example an increase at a particular wavelength previously exhibiting sensitivity, or a general increase of sensitivity encompassing all wavelengths previously exhibiting sensitivity. This second aspect of sensitivity may also be considered as change of sensitivity, encompassing all wavelengths, with a broadband (white) light exposure. A problem encountered in the manufacturing of photoreceptors is maintaining consistent spectral and broadband sensitivity from batch to batch.

Typically, flexible photoreceptor belts are fabricated by depositing the various layers of photoactive coatings onto long webs that are thereafter cut into sheets. The opposite ends of each photoreceptor sheet are overlapped and ultrasonically welded together to form an imaging belt. In order to increase throughput during the web coating operation, the webs to be coated have a width of twice the width of a final belt. After coating, the web is slit lengthwise, and thereafter, transversely cut into predetermined lengths to form photoreceptor sheets of precise dimensions that are eventually welded into belts. The web length in a coating run may be many thousands of feet long, and the coating run may take more than an hour for each layer.

Various types of inorganic photoconductive pigments are known, including pigments based on phthalocyanines. A variety of phthalocyanine-based pigments are suitable for use in photoimaging members, including metal-free phthalocyanines, copper, iron, and zinc phthalocyanines, chloroindium phthalocyanines, hydroxygallium phthalocyanines, certain titanium-based phthalocyanines, such as, for example, titanyl phthalocyanine Type IV, and compositions comprising combinations of the above pigments. U.S. Pat. No. 6,376,141, the entire disclosure of which is incorporated herein by reference, illustrates various compositions comprising combinations of phthalocyanine pigments including hydroxygallium phthalocyanine pigments. Additionally, for example, U.S. Pat. No. 6,713,220, the disclosure of which is totally incorporated herein by reference, discloses a method of preparing a Type V hydroxygallium phthalocyanine.

SUMMARY

Disclosed in embodiments are photoconductors with many of the advantages illustrated herein, such as extended lifetimes of service of, for example, in excess of about 3,000,000 imaging cycles; rapid charge transfer to thereby improve print quality caused by temperature variation in proximity to the photoconductor; excellent electrical characteristics, for example high sensitivity; stable electrical properties; low image ghosting; resistance to charge transport layer cracking upon exposure to the vapor of certain solvents; excellent surface characteristics; improved wear resistance; compatibility with a number of toner compositions; consistent $V_r$ (residual potential) that is substantially flat or no change over a number of imaging cycles as illustrated by the generation of known PIDC (Photoinduced Discharge Curve); stable photogenerating dispersions, extended pot life and excellent optical absorption properties thereof, and the like, and where the photoconductors permit the generation of developed xerographic images with minimal charge deficient spots (CDS).

Further disclosed are drum or layered flexible photoresponsive imaging members.

Moreover, disclosed are layered belt and drum photoresponsive or photoconductive imaging members with mechanically robust and solvent resistant charge transport layers and with rapid transport of charge, especially holes.

Additionally disclosed are flexible imaging members with optional hole blocking layers comprised of metal oxides, phenolic resins, and optional phenolic compounds, and which phenolic compounds contain at least two, and more specifically, two to ten phenol groups or phenolic resins with, for example, a weight average molecular weight of, for example, from about 500 to about 3,000, permitting, for example, a hole blocking layer with excellent efficient electron transport which usually results in a desirable photoconductor low residual potential $V_{low}$.

Also disclosed are photoconductors with rapid charge transporting characteristics, high and stable, with a minimum or no PIDC change, photosensitivity, and which sensitivity in embodiments is about 50 percent higher than similar photoconductors that contain, for example, in the photogenerating layer a hydroxygallium phthalocyanine.

EMBODIMENTS

Aspects of the present disclosure relate to a process which comprises treating a Type I titanyl phthalocyanine with a weak acid having a pKa of at least equal to or greater than about −0.25, dissolving the weak acid treated Type I titanyl phthalocyanine in a solution comprising a trihaloacetic acid and an alkylene halide; adding the mixture comprising the dissolved Type I titanyl phthalocyanine to a solution comprising an alcohol and an alkylene halide thereby precipitating a Type Y titanyl phthalocyanine; treating the Type Y titanyl phthalocyanine with monohalobenzene thereby resulting in a high sensitivity titanyl phthalocyanine; a process wherein the weak acid pKa is from about 0 to about 15, and wherein the weak acid captures the metallic impurities present in the titanyl phthalocyanine Type I; a process where the weak acid pKa is from about 1 to about 10, and wherein the titanyl phthalocyanine obtained is Type V titanyl phthalocyanine; a process where the acid pKa is from about 2 to about 6; a process where the weak acid is selected from the group consisting of acetic acid, phosphoric acid, hydrofluoric acid, monofluoroacetic acid, monochloroacetic acid, monobromoacetic acid, monoiodoacetic acid, dichloroacetic acid, trichloroacetic acid, formic acid, oxalic acid, acetylsalicylic acid, nicotinic acid, pyruvic acid, propionic acid, oxalacetic acid, and mixtures thereof; a process wherein the acid is an acidic aqueous solution containing from about 1 weight percent to about 50 weight percent of the acid; a titanyl phthalocyanine process where the acid is an acidic aqueous solution containing from about 2 weight percent to about 20 weight percent of the acid; a process wherein the ratio of the titanyl phthalocyanine Type I to the weak acid is from about 90/10 to about 30/70, or is from about 80/20 to about 40/60; a process wherein the ratio of the titanyl phthalocyanine Type I to the acid is from about 70/30 to about 50/50 phthalocyanine, and wherein there is removed from the titanyl phthalocyanine Type I metallic impurities prior to its acid pasting thereof, and conversion to the titanyl phthalocyanine Type V; a process wherein the titanyl phthalocyanine Type I is subjected to filtration, isolation, and drying, and wherein there is removed from the titanyl phthalocyanine Type I metallic impurities prior to its acid pasting, and conversion to titanyl phthalocyanine Type V; a process wherein the titanyl phthalocyanine Type Y is subjected to mixing with monohalobenzene followed by filtration, isolation, and drying; a process wherein there results titanyl phthalocyanine Type V with an X-ray diffraction pattern having characteristic diffraction peaks at a Bragg angle 2Θ±0.2° at about 9°, 9.6°, 24°, and 27.2°; a process wherein the solution comprising an alcohol and an alkylene halide has an alcohol to alkylene halide ratio of from about 1/4 (v/v) to about 4/1 (v/v), the titanyl phthalocyanine formed is Type V titanyl phthalocyanine, and wherein the resulting Type V titanyl phthalocyanine has an X-ray diffraction pattern having characteristic diffraction peaks at a Bragg angle 2Θ±0.2° at about 9°, 9.6°, 24°, and 27.2°, and wherein the solution comprising an alcohol and an alkylene halide comprises methanol and methylene chloride; a process wherein the titanyl phthalocyanine is prepared by treating the Type I titanyl phthalocyanine with a weak acid aqueous solution, dissolving the acid treated Type I titanyl phthalocyanine in a solution of trifluoroacetic acid and methylene chloride; precipitating a Type Y titanyl phthalocyanine by adding the solution of trifluoroacetic acid, methylene chloride, and the Type I titanyl phthalocyanine to a solution of methanol and methylene chloride; washing the Type Y titanyl phthalocyanine; and converting the Type Y titanyl phthalocyanine to a Type V titanyl phthalocyanine by treating the Type Y titanyl phthalocyanine with monochlorobenzene; a process for the preparation of titanyl phthalocyanine Type V which comprises mixing a Type I titanyl phthalocyanine with an acid with a pKa of from about 0 to about 12, mixing the resulting acid treated Type I titanyl phthalocyanine in trihaloacetic acid and an alkylene halide; adding the resulting mixture to a solution comprising an alcohol and an alkylene halide thereby precipitating a Type Y titanyl phthalocyanine; mixing the Type Y titanyl phthalocyanine with a monohalobenzene; a process wherein there is removed from the titanyl phthalocyanine Type I metallic impurities, such as titanium oxides prior to its acid pasting and conversion to titanyl phthalocyanine Type V; and a photoconductor comprised of a supporting substrate, a photogenerating layer, and a charge transport layer, and wherein the photogenerating layer contains titanyl phthalocyanine Type V which Type V is prepared by treating Type I titanyl phthalocyanine with a weak acid with a pKa of greater than 0, and more specifically, a pKa weaker than trifluoroacetic acid, mixing the treated Type I titanyl phthalocyanine in a solution comprising a trihaloacetic acid and an alkylene halide; adding the resulting mixture to a solution comprising an alcohol and an alkylene halide thereby precipitating a Type Y titanyl phthalocyanine; treating the Type Y titanyl phthalocyanine with monohalobenzene; a photoconductor containing an optional supporting substrate, a photogenerating layer, and at least one charge transport layer comprised of at least one charge transport component wherein the at least one charge transport component is comprised, for example, of aryl amine molecules of the formula

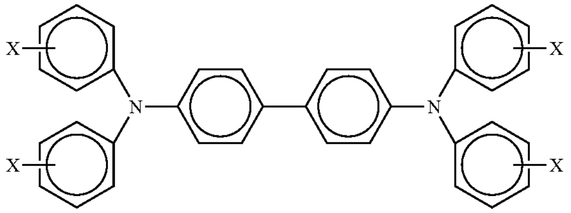

wherein each X is a suitable hydrocarbon like alkyl, alkoxy, aryl, and substituted derivatives thereof; halogen, or mixtures thereof, and wherein the photogenerating layer contains a titanyl phthalocyanine prepared by treating, mixing, contacting and the like a Type I titanyl phthalocyanine with a weak acid; dissolving the treated Type I titanyl phthalocyanine in a solution comprising a trihaloacetic acid and an alkylene halide; adding the mixture comprising the dissolved Type I titanyl phthalocyanine to a solution comprising an alcohol and an alkylene halide thereby precipitating a Type Y titanyl phthalocyanine; treating the Type Y titanyl phthalocyanine with monochlorobenzene to form a Type V titanyl phthalocyanine; and contacting or milling the Type V titanyl phthalocyanine with a monohalobenzene and a polymer binder, and thereafter forming a dispersion of the titanyl phthalocyanine, which dispersion contains a polymer binder and certain chlorinated solvents followed by applying the dispersion to the photoconductor substrate; a photoconductor comprised in sequence of a substrate, a photogenerating layer thereover, and a charge transport layer, and wherein the photogenerating layer contains a titanyl phthalocyanine Type V prepared as illustrated herein where weak acids are selected; and a process for the preparation of a photoconductor which comprises applying or depositing a dispersion of a photogenerating pigment and certain chlorinated solvents on the appropriate photoconductor layer, such as the supporting substrate, the hole blocking layer, the adhesive layer, or the charge transport layer; a photoconductor comprising an optional supporting substrate, a photogenerating layer, and at least one charge transport layer comprised of at least one charge transport component, and wherein the photogenerating layer contains a titanyl phthalocyanine prepared by mixing a Type I titanyl phthalocyanine with a weak acid; dissolving the treated Type I titanyl phthalocyanine in a solution comprising a trihaloacetic acid and an alkylene chloride; adding a mixture comprising the dissolved Type I titanyl phthalocyanine to a solution comprising an alcohol and an alkylene halide thereby precipitating a Type Y titanyl phthalocyanine; treating or mixing the Type Y titanyl phthalocyanine with monochlorobenzene to form a Type V titanyl phthalocyanine; and contacting or milling the Type V titanyl phthalocyanine with a chlorinated solvent of at least one of monohalobenzene, dichloroethane or dichloropropane, and thereafter forming a photogenerating layer dispersion of the titanyl phthalocyanine; a photoconductor comprised in sequence of a substrate, a photogenerating layer thereover, and a charge transport layer, and wherein the photogenerating layer, which is prepared from a titanyl phthalocyanine, a polymer binder, and at least one of monochlorobenzene, dichloroethane or dichloropropane, is deposited on the substrate; and a process for the preparation of a photoconductor member which comprises depositing on a substrate a dispersion of a mixture of a suitable titanyl phthalocyanine photogenerating pigment, and a resin binder, and thereafter coating the photogenerating layer with a charge transport layer.

More specifically, the preparation of the high sensitivity titanyl phthalocyanine involves first the preparation of Type I titanyl phthalocyanine by i) the addition of 1 part of titanium tetrabutoxide to a stirred solution of from about 1 part to about 10 parts, and in embodiments about 4 parts of 1,3-diiminoisoindolene in chloronaphthalene or tetrahydronaphthalene, or a stirred solution of 1 part of 1,3-diiminoisoindolene and 3 parts of o-phthalonitrile in chloronaphthalene or tetrahydronaphthalene; ii) relatively slow application of heat using an appropriate sized heating mantle at a rate of about 1° C. per minute to about 10° C. per minute and, in embodiments, about 5° C. per minute until refluxing occurs at a temperature of about 130° C. to about 180° C. (all temperatures are in Centigrade unless otherwise indicated); iii) removal and collection of the resulting distillate, which was shown by NMR spectroscopy to be butyl alcohol, in a dropwise fashion using an appropriate apparatus, such as a Claisen Head condenser, until the temperature of the reactants reaches from about 190° C. to about 230° C., and in embodiments, about 200° C.; iv) continued stirring at the reflux temperature for a period of about ½ hour to about 8 hours, and in embodiments, about 2 hours; v) cooling the reactants to a temperature of about 130° C. to about 180° C., and in embodiments, about 160° C. by removal of the heat source; vi) filtration of the flask contents through, for example, an M-porosity (10 to 15 microns) sintered glass funnel which was preheated using a solvent, which is capable of raising the temperature of the funnel to about 150° C., for example, a solvent of boiling N,N-dimethylformamide in an amount sufficient to substantially completely cover the bottom of the filter funnel so as to prevent blockage of the funnel; vii) washing the resulting purple solid by slurrying the solid in portions of boiling DMF either in the funnel or in a separate vessel in a ratio of about 1 to about 10, and more specifically; viii) cooling and further washing the solid of impurities by slurrying the washing solid in portions of N,N-dimethylformamide at room temperature, about 25° C., approximately equivalent to about three times blue in color; ix) washing the solid of impurities by slurrying the solid in portions of an organic solvent, such as methanol, acetone, water, and the like, and in this embodiment, methanol, at room temperature (about 25° C.), approximately equivalent to about three times the volume of the solid being washed until the filtrate became light blue in color; x) oven drying the solid in the presence of a vacuum or in air at a temperature of from about 25° C. to about 200° C., and in embodiments at about 70° C. for a period of from about 2 hours to about 48 hours, and in embodiments, for about 24 hours, thereby resulting in the isolation of a shiny purple solid, which was identified as being Type I titanyl phthalocyanine by its X-ray powder diffraction trace.

The Type I titanyl phthalocyanine is then treated with a weak acid by, for example, i) mixing 1 part of the Type I pigment with 10 parts of distilled water and 0.5 part of glacial acetic acid for half an hour; ii) filtration of the mixture to obtain the wet pigment; iii) reslurrying the wet pigment with 20 parts of hot distilled water (>90° C.), filtration, then 20 parts of room temperature distilled water until the conductivity of the water is less than about 10 μS; iv) reslurrying the pigment with 20 parts of methanol, filtration, and drying under vacuum at 70° C. for at least 8 hours.

The weak acid-treated Type I titanyl phthalocyanine can be converted to an intermediate titanyl phthalocyanine form prior to conversion to the high sensitivity titanyl phthalocyanine pigment. "Intermediate" in embodiments refers, for example, to Type Y titanyl phthalocyanine as a separate form prepared prior to obtaining the final desired Type V titanyl phthalocyanine product. For example, to obtain the intermediate form, which is designated as a Type Y titanyl phthalocyanine, the dissolved Type I titanyl phthalocyanine is added to a quenching system comprising an alkyl alcohol, alkyl including, for example, carbon chain lengths of from about 1 to about 12 carbon atoms, and alkylene halides, such as an alkylene chloride. Adding the dissolved Type I titanyl phthalocyanine to the quenching system or quenching mixture causes the Type Y titanyl phthalocyanine to precipitate. Materials suitable as the alkyl alcohol component of the quenching system include, but are not limited to, methanol, ethanol, propanol, butanol, and the like. In embodiments, the alkylene chloride component of the quenching system comprises from about 1 to about 10 carbon atoms. In embodiments, the quenching system comprises methanol and methylene chloride. The quenching system comprises an alkyl alcohol to alkylene chloride ratio of from about 1/4 to about 4/1 (v/v). In other embodiments, the ratio of alkyl alcohol to alkylene chloride is from about 1/1 to about 3/1 (v/v). In an embodiment, the quenching system comprises methanol and methylene chloride in a ratio of about 1/1 (v/v). In another embodiment, the quenching system comprises methanol and methylene chloride in a ratio of about 3/1 (v/v). In embodiments, the dissolved Type I titanyl phthalocyanine is added to the quenching system at a rate of from about 1 milliliter/minute to about 100 milliliters/minute, and the quenching system is maintained at a temperature of from about 0° C. to about −25° C. during quenching. In a further embodiment, the quenching system is maintained at a temperature of from about 0° C. to about −25° C. for a period of from about 0.1 hour to about 8 hours after addition of the dissolved Type I titanyl phthalocyanine solution.

Following precipitation of the Type Y titanyl phthalocyanine, the precipitates may be washed with any suitable solution including, for example, methanol, cold deionized water, hot deionized water, and the like. Generally, washing the precipitate is also accompanied by filtration. A wet cake containing Type Y titanyl phthalocyanine and water is obtained with the water content varying from about 30 to about 70 weight percent of the wet cake. The Type V titanyl phthalocyanine can then be generated by treating and washing the obtained intermediate Type Y titanyl phthalocyanine with a weak acid and a halo, such as, for example, monochlorobenzene; thereafter drying the resulting wet cake after redispersing in monochlorobenzene, filtering and oven-drying at a temperature of from about 60° C. to about 85° C. to provide the resultant Type V titanyl phthalocyanine. The monochlorobenzene treatment may occur over a period of about 1 hour to about 24 hours. In one embodiment, the monochlorobenzene treatment is accomplished for a period of about five hours.

While not being desired to be limited by theory, it is believed that the weak acid dissolves metal impurities, such as organic titanates, to form soluble salts thereof, and which salts can be subsequently removed during washing, and where the titanyl phthalocyanine is substantially free of dissolution in the weak acid. In this manner, there can be formed layered photoconductors that when incorporated into printing machines result in final prints with minimal CDSs.

Weak acids include in embodiments those acids weaker than trifluoroacetic acid, that is where the weak acids have a pKa of not less than −0.25, and more specifically, with a pKa of from about 0 to about 10, or from about 1 to about 6. For example, acetic acid that has a pKa of 4.76 is about 100,000 fold less acidic than trifluoroacetic acid that has a pKa of −0.25. Specific examples of weak acids are acetic acid with a pKa of 4.76, phosphoric acid with a pKa of 2.12, 7.21 and 12.67, hydrofluoric acid with a pKa of 3.17, monohaloacetic acid with a pKa of 2.66 (monofluoroacetic acid), 2.86 (monochloroacetic acid and monobromoacetic acid), and 3.12 (monoiodoacetic acid), dichloroacetic acid with a pKa of 1.29, trichloroacetic acid with a pKa of 0.65, formic acid with a pKa of 3.77, oxalic acid, and oxalacetic acid.

Chlorinated solvents selected for the photogenerating dispersion include monochlorobenzene, dichloroalkanes, and more specifically, 1,2-dichloroethane, 1,2-dichloropropane, 1,3-dichloropropane, 1,2-dichlorobutane, 2,3-dichlorobutane, 1,3-dichlorobutane, and mixtures thereof. The photogenerating dispersion is comprised, for example, of a mixture containing from about 1 weight percent to about 10 weight percent of a photogenerating pigment, from 80 weight percent to about 98 weight percent of chlorinated solvent, and from 1 weight percent to about 10 weight percent polymer binder. More specifically, the photogenerating mixture contains from about 2 weight percent to about 6 weight percent of a TiOPc Type V photogenerating pigment, from about 90 weight percent to about 96 weight percent of chlorinated solvent, and from about 2 weight percent to about 6 weight percent of polymer binder. The specific chlorinated solvents selected preserve the high photosensitivity of the TiOPc pigment, such as Type V or Type IV, in dispersion mixture for more than 100 hours, such as from about 101 to about 540 hours, whereas when nonchlorinated solvents are selected, such as tetrahydrofuran, dioxolane, can cause a serious deterioration of photosensitivity, up to an extent of a 50 percent loss. This rapid loss may impose a severe time constraint on photoreceptor manufacturing processes as the useful potlife of a pigment dispersion is rather limited as disclosed herein. It is believed that the chlorinated solvents disclosed do not substantially alter the crystal structure of the high photosensitivity TiOPc. Also, it is generally known that the photosensitivity of phthalocyanines, including TiOPc, depends on its crystal structure. Tetrahydrofuran and dioxolane can convert the high sensitivity crystal structure into a lower sensitivity form. The photoreceptors incorporating a high photosensitivity TiOPc pigment are particularly suitable for high-speed electrophotography printing applications as less exposure energy from a laser ROS (raster-optical scanning) system is needed to image them.

The photogenerating layer in embodiments is comprised of high photosensitivity titanyl phthalocyanines prepared as illustrated herein. In embodiments, the Type V phthalocyanine can be generated by contacting a Type I titanyl phthalocyanine with a weak acid; dissolving the treated Type I titanyl phthalocyanine in a solution comprising a trihaloacetic acid and an alkylene halide; adding the mixture comprising the dissolved Type I titanyl phthalocyanine to a solution comprising an alcohol and an alkylene halide thereby precipitating a Type Y titanyl phthalocyanine; and mixing the Type Y titanyl phthalocyanine with monochlorobenzene to form a Type V titanyl phthalocyanine.

With further respect to the titanyl phthalocyanines selected for the photogenerating layer, such phthalocyanines exhibit a crystal phase that is distinguishable from other known titanyl phthalocyanine polymorphs, and are designated as Type V polymorphs prepared as illustrated herein wherein weak acids are selected.

In one embodiment, the process comprises (a) treating a Type I titanyl phthalocyanine with a weak acid; (b) dissolving the weak acid treated Type I titanyl phthalocyanine in a suitable solvent; (c) adding the solvent solution comprising the dissolved Type I titanyl phthalocyanine to a quenching solvent system to precipitate an intermediate titanyl phthalocyanine (designated as a Type Y titanyl phthalocyanine); and (d) treating the resultant Type Y phthalocyanine with a halo, such as, for example, monochlorobenzene to obtain a resultant high sensitivity titanyl phthalocyanine, which is designated herein as a Type V titanyl phthalocyanine. The quenching solvents system, to which the solution comprising the dissolved Type I titanyl phthalocyanine is added, comprises, for example, an alkyl alcohol and an alkylene halide.

The process further provides a titanyl phthalocyanine having a crystal phase distinguishable from other known titanyl phthalocyanines. The titanyl phthalocyanine Type V prepared by a process according to the present disclosure is distinguishable from, for example, Type IV titanyl phthalocyanines in that a Type V titanyl phthalocyanine exhibits an X-ray powder diffraction spectrum having four characteristic peaks at 9°, 9.6°, 24°, and 27.2°, while Type IV titanyl phthalocyanines typically exhibit only three characteristic peaks at 9.6°, 24°, and 27.2°.

A number of Type I titanyl phthalocyanines may be selected for the generation of the Type V titanyl phthalocyanine, such as the Type I titanyl phthalocyanines prepared as illustrated in U.S. Pat. Nos. 5,153,094; 5,166,339; 5,189,155; and 5,189,156, the disclosures of which are totally incorporated herein by reference. Specifically, a Type I titanyl phthalocyanine may be prepared, in embodiments, by the reaction of $DI^3$ (1,3-diiminoisoindolene) and tetrabutoxide in the presence of 1-chloronaphthalene solvent, whereby there is obtained a crude Type I titanyl phthalocyanine, which is subsequently purified up to about a 99.5 percent purity by washing with, for example, dimethylformamide. Yet more specifically, a Type I titanyl phthalocyanine may be prepared, in embodiments, by the reaction of $DI^3$ (1,3-diiminoisoindolene), o-phthalonitrile and tetrabutoxide in the presence of 1-tetrahydronaphthalene solvent, whereby there is obtained a crude Type I titanyl phthalocyanine, which is subsequently purified up to about a 99.5 percent purity by washing with, for example, dimethylformamide and ammonium aqueous solution.

In another embodiment, for example, a Type I titanyl phthalocyanine can also be prepared by i) the addition of 1 part titanium tetrabutoxide to a stirred solution of from about 3 parts to about 7 parts, and in embodiments about 4 parts of 1,3-diiminoisoindolene; ii) heating using an appropriately sized heating mantle at a rate of about 1° C. per minute to about 10° C. per minute, and, in embodiments, about 5° C. per minute until refluxing occurs at a temperature of about 140° C. to about 170° C. (all temperatures are in Centigrade unless otherwise indicated); iii) removal and collection of the resulting distillate, which was shown by NMR spectroscopy to be butyl alcohol, in a dropwise fashion using an appropriate apparatus, such as a Claisen Head condenser, until the temperature of the reactants reaches from about 200° C. to about 215° C., and in embodiments about 200° C.; iv) continued stirring at the reflux temperature for a period of about 2 hours to about 7 hours, and in embodiments, about 3 hours; v) cooling the reactants to a temperature of about 130° C. to about 180° C., and in embodiments, about 155° C. by removal of the heat source; vi) filtration of the flask contents through, for example, an M-porosity (10 to 15 microns) sintered glass funnel which was preheated using a solvent, which is capable of raising the temperature of the funnel to about 150° C., for example, a solvent of boiling N,N-dimethylformamide in an amount sufficient to substantially completely cover the bottom of the filter funnel so as to prevent blockage of the funnel; vii) washing the resulting purple solid by slurrying the solid in portions of boiling DMF either in the funnel or in a separate vessel in a ratio of about 1 to about 10, and more specifically; viii) cooling and further washing the solid of impurities by slurrying the washing solid in portions of N,N-dimethylformamide at room temperature, about 25° C., approximately equivalent to about three times blue in color; ix) washing the solid of impurities by slurrying the solid in portions of an organic solvent, such as methanol, acetone, water, and the like, and in this embodiment, methanol, at room temperature (about 25° C.), approximately equivalent to about three times the volume of the solid being washed until the filtrate became light blue in color; x) oven drying the solid in the presence of a vacuum or in air at a temperature of from about 25° C. to about 200° C., and in embodiments at about 70° C. for a period of from about 2 hours to about 48 hours, and in embodiments, for about 24 hours, thereby resulting in the isolation of a shiny purple solid, which was identified as being Type I titanyl phthalocyanine by its X-ray powder diffraction trace. Subsequently, the Type I obtained is washed in a weak acid, acid pasted, and then converted to Type V titanyl phthalocyanine.

In still another embodiment, a Type I titanyl phthalocyanine may be prepared by (1) reacting a $DI^3$ with a titanium tetra alkoxide, such as, for example, titanium tetrabutoxide at a temperature of about 195° C. for about two hours; (ii) filtering the contents of the reaction to obtain a resulting solid; (iii) washing the solid with dimethylformamide (DMF); (iv) washing with four percent ammonium hydroxide; (v) washing with deionized water; (vi) washing with methanol; (vii) reslurrying the washes and filtering; and (viii) drying at about 70° C. under vacuum to obtain a Type I titanyl phthalocyanine.

In a process embodiment for preparing a high sensitivity phthalocyanine in accordance with the present disclosure, a Type I titanyl phthalocyanine is treated with a weak acid that has a pKa not less than about −0.25. After the weak acid treatment, the resulting pigment is washed with hot distilled water, cold distilled water, and methanol. Generally, washing the pigment is also accompanied by filtration.

The weak acid treated Type I titanyl phthalocyanine is dissolved in a suitable solvent. In embodiments, the weak acid treated Type I titanyl phthalocyanine is dissolved in a solvent comprising a trihaloacetic acid and an alkylene halide. The alkylene halide comprises, in embodiments, from about one to about six carbon atoms. An example of a suitable trihaloacetic acid includes, but is not limited to, trifluoroacetic acid. In one embodiment, the solvent for dissolving the Type I titanyl phthalocyanine comprises trifluoroacetic acid and methylene chloride. In embodiments, the trihaloacetic acid is present in an amount of from about one volume part to about 100 volume parts of the solvent, and the alkylene halide is present in an amount of from about one volume part to about 100 volume parts of the solvent. The solvent in embodiments comprises methylene chloride and trifluoroacetic acid in a volume-to-volume ratio of about 4 to 1. The Type I titanyl phthalocyanine is dissolved in the solvent by stirring for an effective period of time, such as, for example, for about 30 seconds to about 24 hours, at room temperature. The Type I titanyl phthalocyanine may be dissolved in the solvent in either air or in an inert atmosphere (argon or nitrogen).

The Type I titanyl phthalocyanine can be converted to an intermediate titanyl phthalocyanine form as illustrated herein and prior to conversion to the high sensitivity titanyl phthalocyanine pigment. For example, to obtain the intermediate form, which is designated as a Type Y titanyl phthalocyanine, the dissolved Type I titanyl phthalocyanine is added to a quenching system comprising an alkyl alcohol, alkyl including, for example, carbon chain lengths of from about 1 to about 12 carbon atoms, and alkylene halides, such as an alkylene chloride. Adding the dissolved Type I titanyl phthalocyanine to the quenching system or quenching mixture causes the Type Y titanyl phthalocyanine to precipitate. Materials suitable as the alkyl alcohol component of the quenching system include, but are not limited to, methanol, ethanol, propanol, butanol, and the like. In embodiments, the alkylene chloride component of the quenching system comprises from about 1 to about 10 carbon atoms. The quenching system comprises an alkyl alcohol, and alkylene chloride in a ratio of from about 1/4 to about 4/1 (v/v). Also, in embodiments, the quenching system comprises methanol and methylene chloride in a ratio of about 1/1 (v/v). In another embodiment, the quenching system comprises an alcohol and methylene chloride in a ratio of about 3/1 (v/v). In embodiments, the dissolved Type I titanyl phthalocyanine is added to the quenching system at a rate of from about 1 milliliter/minute to about 100 milliliters/minute, and the quenching system is maintained at a temperature of from about 0° C. to about −25° C. during quenching. In a further embodiment, the quenching system is maintained at a temperature of from about 0° C. to about −25° C. for a period of from about 0.1 hour to about 8 hours after addition of the dissolved Type I titanyl phthalocyanine solution.

Following precipitation of the Type Y titanyl phthalocyanine, the precipitates may be washed with a suitable solution including, for example, methanol, cold deionized water, hot deionized water, and the like. Generally, washing the precipitate is also accompanied by filtration. A wet cake containing Type Y titanyl phthalocyanine and water is obtained with the water content varying from about 30 to about 70 weight percent of the wet cake. The Type V titanyl phthalocyanine is obtained by treating the obtained intermediate Type Y titanyl phthalocyanine with a halo, such as, for example, monochlorobenzene. The Type Y titanyl phthalocyanine wet cake may be redispersed in monochlorobenzene, filtered, and oven dried at a temperature of from about 60° C. to about 85° C. to provide the resultant Type V titanyl phthalocyanine. The monochlorobenzene treatment may occur over a period of about 1 hour to about 24 hours. In one embodiment, the monochlorobenzene treatment is accomplished for a period of about five hours.

A titanyl phthalocyanine obtained in accordance with processes of the present disclosure, which is designated as a Type V titanyl phthalocyanine, exhibits an X-ray powder diffraction spectrum distinguishable from a number of other known titanyl phthalocyanine polymorphs. A Type V titanyl phthalocyanine obtained exhibits, in embodiments, an X-ray diffraction spectrum having four characteristic peaks at 9°0, 9.6°, 24°, and 27.2°. A titanyl phthalocyanine prepared by a process in accordance with the present disclosure may have a particle size diameter of from about 10 nanometers to about 500 nanometers. Particle size may be controlled or affected by the quenching rate when adding the dissolved Type I titanyl phthalocyanine to the quenching system and the composition of the quenching system.

Generally, the thickness of the photogenerating layer depends on a number of factors, including the thicknesses of the other layers, and the amount of photogenerating material contained in the photogenerating layer. Accordingly, this layer can be of a thickness of, for example, from about 0.05 micron to about 30 microns, or to about 10 microns, and more specifically, from about 0.25 micron to about 2 microns when, for example, the photogenerating compositions are present in an amount of from about 30 to about 75 percent by volume. The maximum thickness of this layer in embodiments is dependent primarily upon factors, such as photosensitivity, electrical properties, and mechanical considerations. The photogenerating layer binder resin includes those polymers as disclosed in U.S. Pat. No. 3,121,006, the disclosure of which is totally incorporated herein by reference, and is present in various suitable amounts, for example from about 1 to about 50 weight percent, and more specifically, from about 1 to about 10 weight percent, and which resin may be selected from a number of known polymers such as poly (vinyl butyral), poly(vinyl carbazole), polyesters, polycarbonates, poly(vinyl chloride), polyacrylates and methacrylates, copolymers of vinyl chloride and vinyl acetate, phenolic resins, polyurethanes, poly(vinyl alcohol), polyacrylonitrile, polystyrene, and the like. It is desirable to select a coating solvent that does not substantially disturb or adversely affect the other previously coated layers of the device. Examples of coating solvents for the photogenerating layer are ketones, alcohols, aromatic hydrocarbons, halogenated aliphatic/aromatic hydrocarbons, ethers, amines, amides, esters, and the like. Specific examples of coating solvents are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethyl formamide, dimethyl acetamide, butyl acetate, ethyl acetate, methoxyethyl acetate, and the like.

In embodiments, the photogenerating layer may contain in addition to the high sensitivity titanyl phthalocyanine other known photogenerating pigments like metal phthalocyanines, metal free phthalocyanines, alkylhydroxyl gallium phthalocyanines, hydroxygallium phthalocyanines, chlorogallium phthalocyanines, perylenes, especially bis(benzimidazo)perylene, titanyl phthalocyanines, and the like, and more specifically, vanadyl phthalocyanines, Type V hydroxygallium phthalocyanines, and inorganic components such as selenium, selenium alloys, and trigonal selenium. Generally, in embodiments the photoconductor is comprised of the above photogenerating layer deposited on a supporting substrate, and which layer can be situated between the at least one charge transport layer and the substrate.

The thickness of the photoconductor substrate layer depends on many factors, including economical considerations, electrical characteristics, and the like, thus this layer may be of substantial thickness, for example over 3,000 microns, such as from about 300 to about 700 microns, or of a minimum thickness. In embodiments, the thickness of this layer is from about 75 microns to about 300 microns, or from about 100 microns to about 150 microns.

The substrate may be opaque or substantially transparent, and may comprise any suitable material inclusive of known materials with suitable mechanical properties. Accordingly, the substrate may comprise a layer of an electrically nonconductive or conductive material such as an inorganic or an organic composition. As electrically nonconducting materials, there may be employed various resins known for this purpose including polyesters, polycarbonates, polyamides, polyurethanes, and the like, which are flexible as thin webs. An electrically conducting substrate may be any suitable metal of, for example, aluminum, nickel, steel, copper, and the like, or a polymeric material, as described above, filled with an electrically conducting substance, such as carbon, metallic powder, and the like, or an organic electrically conducting material. The electrically insulating, or conductive substrate may be in the form of an endless flexible belt, a web, a rigid cylinder, a sheet, and the like. The thickness of the substrate layer depends on numerous factors, including strength desired and economical considerations. For a drum, as disclosed in a copending application referenced herein, this layer may be of a substantial thickness of, for example, up to many centimeters or of a minimum thickness of less than a millimeter. Similarly, a flexible belt may be of a substantial thickness, for example about 250 micrometers, or of a minimum thickness of less than 50 micrometers, provided there are no adverse effects on the final electrophotographic device.

Illustrative examples of substrates are as illustrated herein, and can comprise a layer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass, or the like. The substrate may be flexible, seamless, or rigid, and may have a number of many different configurations, such as for example, a plate, a cylindrical drum, a scroll, an endless flexible belt, and the like. In embodiments, the substrate is in the form of a seamless flexible belt. In some situations, it may be desirable to coat on the back of the substrate, particularly when the substrate is a flexible organic polymeric material, an anticurl layer, such as for example, polycarbonate materials commercially available as MAKROLON®.

Various resins can be used as electrically nonconducting substrate materials, including, but not limited to, polyesters, polycarbonates, polyamides, polyurethanes, and the like. Examples of suitable substrate materials include, but are not limited to, a commercially available biaxially oriented polyester known as MYLAR™, available from E.I. DuPont de Nemours & Company, MELINEX™, available from ICI Americas Inc., or HOSTAPHAN™, available from American Hoechst Corporation. Other materials of which the substrate may be comprised include polymeric materials, such as polyvinyl fluoride, available as TEDLAR™ from E.I. DuPont de Nemours & Company, polyethylene and polypropylene, available as MARLEX™ from Phillips Petroleum Company, polyphenylene sulfide, RYTON™, available from Phillips Petroleum Company, and polyimides, available as KAPTON™ from E.I. DuPont de Nemours & Company. The photoreceptor can also be coated on an insulating plastic drum, provided a conducting ground plane has previously been coated on its surface, as described above. Such substrates can either be seamed or seamless.

When a conductive substrate is employed, any suitable conductive material can be selected. For example, the conductive material can include, but is not limited to, metal flakes, powders or fibers, such as aluminum, titanium, nickel, chromium, brass, gold, stainless steel, carbon black, graphite, or the like, in a binder resin including metal oxides, sulfides, silicides, quaternary ammonium salt compositions, conductive polymers, such as polyacetylene or its pyrolysis, and molecular doped products, charge transfer complexes, polyphenyl silane, and molecular doped products from polyphenyl silane. A conducting plastic drum or a conducting metal drum of a material, such as aluminum, can be selected as the substrate.

A number of known charge transport components can be selected for the charge transport layer, such as aryl amines, which layer is generally of a thickness of from about 5 microns to about 75 microns, and more specifically, of a thickness of from about 10 microns to about 40 microns, including molecules of the following formulas

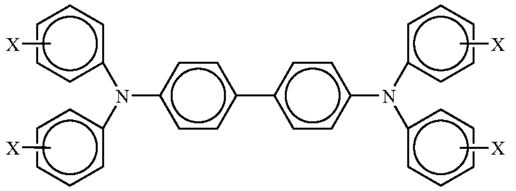

and

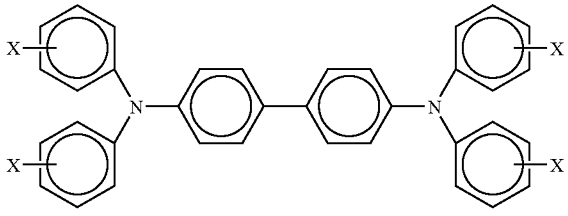

wherein each X is a suitable hydrocarbon like alkyl, alkoxy, aryl, and substituted derivatives thereof; a halogen, and especially those substituents selected from the group consisting of Cl and $CH_3$; molecules of the following formula

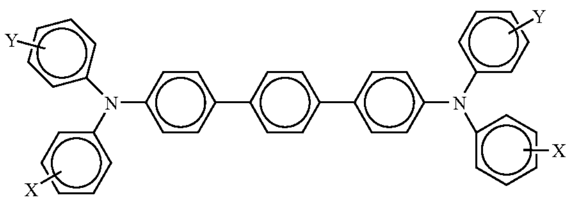

wherein X and Y are independently alkyl, alkoxy, aryl, a halogen, or mixtures thereof. Alkyl and alkoxy contain, for example, from 1 to about 25 carbon atoms, and more specifically, from 1 to about 12 carbon atoms, such as methyl, ethyl, propyl, butyl, pentyl, and the corresponding alkoxides. Aryl can contain from 6 to about 36 carbon atoms, such as phenyl, and the like. Halogen includes chloride, bromide, iodide and fluoride. Substituted alkyls, alkoxys, and aryls can also be selected in embodiments.

Examples of specific aryl amines include N,N'-diphenyl-N,N'-bis(alkylphenyl)-1,1-biphenyl-4,4'-diamine wherein alkyl is selected from the group consisting of methyl, ethyl, propyl, butyl, hexyl, and the like; N,N'-diphenyl-N,N'-bis(halophenyl)-1,1'-biphenyl-4,4'-diamine wherein the halo substituent is a chloro substituent; N,N'-bis(4-butylphenyl)-N,N'-di-p-tolyl-[p-terphenyl]-4,4"-diamine, N,N'-bis(4-butylphenyl)-N,N'-di-m-tolyl-[p-terphenyl]-4,4"-diamine, N,N'-bis(4-butylphenyl) -N,N'-di-o-tolyl-[p-terphenyl]-4,4"-diamine, N,N'-bis(4-butylphenyl)-N,N'-bis-(4-isopropylphenyl)-[p-terphenyl]-4,4"-diamine, N,N'-bis(4-butylphenyl)-N,N'-bis-(2-ethyl-6-methylphenyl)-[p-terphenyl]-4,4"-diamine, N,N'-bis(4-butylphenyl)-N,N'-bis-(2,5-dimethylphenyl)-[p-terphenyl]-4,4"-diamine, N,N'-diphenyl-N,N'-bis(3-chlorophenyl)-[p-terphenyl]-4,4"-diamine, and the like. Other known charge transport layer molecules can be selected, reference for example U.S. Pat. Nos. 4,921,773 and 4,464,450, the disclosures of which are totally incorporated herein by reference.

The charge transport layer or layers, and more specifically, a first charge transport in contact with the photogenerating layer, and thereover a top or second charge transport overcoating layer may comprise the illustrated charge transporting small molecules dissolved or molecularly dispersed in a film forming electrically inert polymer such as a polycarbonate. In embodiments, "dissolved" refers, for example, to forming a solution in which the small molecule is dissolved in the polymer to form a homogeneous phase; and "molecularly dispersed in embodiments" refers, for example, to charge transporting molecules dispersed in the polymer, the small molecules being dispersed in the polymer on a molecular scale.

Examples of hole transporting molecules for the at least one charge transport layer, such as the first and second charge transport layer, are as indicated herein and include, for example, known hole transport components; aryl amines such as N,N'-diphenyl-N,N'-bis(3-methylphenyl)-(1,1'-biphenyl)-4,4'-diamine, N,N'-diphenyl-N,N-bis(4-methylphenyl)-1,1'-biphenyl-4,4'-diamine, N,N'-diphenyl-N,N -bis(2-methylphenyl)-1,1'-biphenyl-4,4'-diamine, N,N'-bis(4-butylphenyl)-N,N'-di-p -tolyl-[p-terphenyl]-4,4"-diamine, N,N'-bis(4-butylphenyl)-N,N'-di-m-tolyl-[p-terphenyl]-4,4"-diamine, N,N'-bis(4-butylphenyl)-N,N'-di-o-tolyl-[p-terphenyl]-4,4"-diamine, N,N'-bis(4-butylphenyl)-N,N'-bis-(4-isopropylphenyl)-[p-terphenyl]-4,4"-diamine, N,N'-bis(4-butylphenyl)-N,N'-bis-(2-ethyl-6-methylphenyl)-[p-terphenyl]-4,4"-diamine, N,N'-bis(4-butylphenyl)-N,N'-bis-(2,5-dimethylphenyl)-[p-terphenyl]-4,4"-diamine, N,N'-diphenyl -N,N'-bis(3-chlorophenyl)-[p-terphenyl]-4,4"-diamine, optionally mixtures thereof, and the like. In embodiments, to minimize or avoid cycle-up in equipment, such as printers, with high throughputs, it is sometimes desirable that the charge transport layer be substantially free (less than about two percent) of a di or triamino-triphenyl methane. The electrically active small molecule charge transporting compounds are dissolved or molecularly dispersed in electrically inactive polymeric film forming materials. A small molecule charge transporting compound that permits injection of holes into the photogenerating layer with high efficiency, and transports them across the charge transport layer with short transit times specifically includes N,N'-diphenyl-N,N'-bis(3-methylphenyl)-(1,1'-biphenyl)-4,4'-diamine, N,N'-diphenyl-N,N-bis(4-methylphenyl)-1,1'-biphenyl-4,4'-diamine, N,N'-diphenyl-N,N-bis(2-methylphenyl)-1,1'-biphenyl-4,4'-diamine, N,N'-bis(4-butylphenyl)-N,N'-di-p-tolyl-[p-terphenyl]-4,4"-diamine, N,N'-bis(4-butylphenyl)-N,N'-di-m-tolyl-[p-terphenyl]-4,4"-diamine, N,N'-bis(4-butylphenyl)-N,N'-di-o-tolyl-[p-terphenyl]-4,4"-diamine, N,N'-bis(4-butylphenyl) -N,N'-bis-(4-isopropylphenyl)-[p-terphenyl]-4,4"-diamine, N,N'-bis(4-butylphenyl)-N,N'-bis-(2-ethyl-6-methylphenyl)-[p-terphenyl]-4,4"-diamine, N,N'-bis(4-butylphenyl)-N,N'-bis-(2,5-dimethylphenyl)-[p-terphenyl]-4,4"-diamine, or N,N'-diphenyl-N,N'-bis(3-chlorophenyl)-[p-terphenyl]-4,4"-diamine. If desired, the charge transport material in the charge transport layer may comprise a polymeric charge transport material, or a combination of a small molecule charge transport material and a polymeric charge transport material.

The charge transport layer should be an insulator to the extent that the electrostatic charge placed on the hole transport layer is not conducted in the absence of illumination at a rate sufficient to prevent formation and retention of an electrostatic latent image thereon. In general, the ratio of the thickness of the charge transport layer to the photogenerating layer can be maintained from about 2:1 to about 200:1, and in some instances as great as 400:1. The charge transport layer is substantially nonabsorbing to visible light or radiation in the region of intended use, but is electrically "active" in that it allows the injection of photogenerated holes from the photoconductive layer, that is the photogenerating layer, and allows these holes to be transported through itself to selectively discharge a surface charge on the surface of the active layer.

The thickness of the charge transport overcoat layer selected depends, for example, upon the abrasiveness of the charging (bias charging roll), cleaning (blade or web), development (brush), transfer (bias transfer roll), and the like in the system employed, and can be up to about 10 micrometers. In embodiments, this thickness for each layer is from about 1 micrometer to about 5 micrometers. Various suitable and conventional methods may be used to mix, and thereafter apply the overcoat layer coating mixture to the photogenerating layer. Typical application techniques include spraying, dip coating, roll coating, wire wound rod coating, and the like. Drying of the deposited coating may be effected by any suitable conventional technique such as oven drying, infrared radiation drying, air drying, and the like. The dried overcoating layer of this disclosure should transport holes during imaging, and should not have too high a free carrier concentration. Free carrier concentration in the overcoat increases the dark decay.

The overcoat layer or layers can comprise the same components as the charge transport layer wherein the weight ratio between the charge transporting small molecule, and the suitable electrically inactive resin binder is less, such as for example, from about 0/100 to about 60/40, or from about 20/80 to about 40/60.

Examples of the binder materials selected for the charge transport layers include components, such as those described in U.S. Pat. No. 3,121,006, the disclosure of which is totally incorporated herein by reference. Specific examples of polymer binder materials include polycarbonates, polyarylates, acrylate polymers, vinyl polymers, cellulose polymers, polyesters, polysiloxanes, polyamides, polyurethanes, poly(cyclo olefins), epoxies, and random or alternating copolymers thereof. In embodiments, electrically inactive binders are comprised of polycarbonate resins with, for example, a molecular weight of from about 20,000 to about 100,000, and more specifically, with a molecular weight $M_w$ of from about 50,000 to about 100,000. Examples of polycarbonates are poly(4,4'-isopropylidene-diphenylene)carbonate (also referred to as bisphenol-A-polycarbonate), poly(4,4'-cyclohexylidinediphenylene)carbonate (referred to as bisphenol-Z polycarbonate), poly(4,4'-isopropylidene-3,3'-dimethyl-diphenyl)carbonate (also referred to as bisphenol-C-polycarbonate), and the like.

The optional hole blocking or undercoat layer for the imaging members of the present disclosure can contain a number of components, including known hole blocking components, such as amino silanes, doped metal oxides, TiSi, a metal oxide like titanium, chromium, zinc, tin, and the like; a mixture of phenolic compounds and a phenolic resin, or a mixture of two phenolic resins; and optionally a dopant such as $SiO_2$. The phenolic compounds usually contain at least two phenol groups, such as bisphenol A (4,4'-isopropylidenediphenol), E (4,4'-ethylidenebisphenol), F (bis(4-hydroxyphenyl)methane), M (4,4'-(1,3-phenylenediisopropylidene)bisphenol), P (4,4'-(1,4-phenylenediisopropylidene)bisphenol), S (4,4'-sulfonyldiphenol), Z (4,4'-cyclohexylidenebisphenol); hexafluorobisphenol A (4,4'-(hexafluoro isopropylidene) diphenol), resorcinol, hydroxyquinone, catechin, and the like.

The hole blocking layer can be, for example, comprised of from about 20 weight percent to about 80 weight percent, and more specifically, from about 55 weight percent to about 65 weight percent of a suitable component like a metal oxide, such as $TiO_2$, from about 20 weight percent to about 70 weight percent, and more specifically, from about 25 weight percent to about 50 weight percent of a phenolic resin; from about 2 weight percent to about 20 weight percent, and more specifically, from about 5 weight percent to about 15 weight percent of a phenolic compound, and yet more specifically, containing at least two phenolic groups, such as bisphenol S, and from about 2 weight percent to about 15 weight percent, and more specifically, from about 4 weight percent to about 10 weight percent of a plywood suppression dopant, such as $SiO_2$. The hole blocking layer coating dispersion can, for example, be prepared as follows. The metal oxide/phenolic resin dispersion is first prepared by ball milling or dynomilling until the median particle size of the metal oxide in the dispersion is less than about 10 nanometers, for example from about 5 to about 9 nanometers. To the above dispersion, a phenolic compound and dopant are added followed by mixing. The hole blocking layer coating dispersion can be applied by dip coating or web coating, and the layer can be thermally cured after coating. The hole blocking layer resulting is, for example, of a thickness of from about 0.01 micron to about 30 microns, and more specifically, from about 0.1 micron to about 8 microns. Examples of phenolic resins include formaldehyde polymers with phenol, p-tert-butylphenol, cresol, such as VARCUM® 29159 and 29101 (available from OxyChem Company), and DURITE® 97 (available from Borden Chemical), formaldehyde polymers with ammonia, cresol and phenol, such as VARCUM® 29112 (available from OxyChem Company), formaldehyde polymers with 4,4'-(1-methylethylidene)bisphenol, such as VARCUM™ 29108 and 29116 (available from OxyChem Company), formaldehyde polymers with cresol and phenol, such as VARCUM® 29457 (available from OxyChem Company), DURITE® SD-423A, SD-422A (available from Borden Chemical), or formaldehyde polymers with phenol and p-tert-butylphenol, such as DURITE® ESD 556C (available from Border Chemical). The optional hole blocking layer may be applied to the substrate. Any suitable and conventional blocking layer capable of forming an electronic barrier to holes between the adjacent photoconductive layer (or electrophotographic imaging layer) and the underlying conductive surface of the substrate may be selected.

In embodiments, a suitable known adhesive layer, usually situated between the hole blocking layer and the photogenerating layer, can be selected for the photoconductor. Typical adhesive layer materials include, for example, polyesters, polyurethanes, and the like. The adhesive layer thickness can vary, and in embodiments is, for example, from about 0.05 micrometer (500 Angstroms) to about 0.3 micrometer (3,000 Angstroms). The adhesive layer can be deposited on the hole blocking layer by spraying, dip coating, roll coating, wire wound rod coating, gravure coating, Bird applicator coating, and the like. Drying of the deposited coating may be effected by, for example, oven drying, infrared radiation drying, air drying, and the like.

As adhesive layer component examples, there can be selected various known substances inclusive of polyesters, copolyesters, polyamides, poly(vinyl butyral), poly(vinyl alcohol), polyurethane, and polyacrylonitrile. This layer is, for example, of a thickness of from about 0.001 micron to about 1 micron, or from about 0.1 to about 0.5 micron. Optionally, this layer may contain effective suitable amounts, for example from about 1 to about 10 weight percent, of conductive and nonconductive particles, such as zinc oxide, titanium dioxide, silicon nitride, carbon black, and the like, to provide, for example, in embodiments of the present disclosure further desirable electrical and optical properties.

Aspects of the present disclosure relate to a photoconductive imaging member comprised of a supporting substrate, a photogenerating layer thereover, and thereover the photogenerating layer at least one charge transport layer, such as from 1 to about 7 layers, from 2 to about 4 layers, one layer, two layers, and the like, and an overcoating charge transport layer; a photoconductive member with a photogenerating layer of a thickness of from about 0.1 to about 10 microns; at least one transport layer each of a thickness of from about 5 to about 100 microns; an imaging method and an imaging apparatus containing a charging component; a development component, a transfer component, and a fixing component, and wherein the apparatus contains a photoconductive imaging member comprised of a supporting substrate, and thereover a layer comprised of a Type V titanyl phthalocyanine photogenerating pigment and a charge transport layer or layers, and thereover an overcoating charge transport layer; a member wherein the photogenerating layer contains the TiOPc photogenerating pigment present in an amount of from about 5 to about 95 weight percent; a member wherein the thickness of the photogenerating layer is from about 0.1 to about 4 microns; a member wherein the photogenerating layer contains a polymer binder the same as or similar to the charge transport layer binder; a member wherein the photogenerating layer binder is present in an amount of from about 55 to about 95 percent by weight, and wherein the total of all layer components is about 100 percent; a member wherein the photogenerating component is Type V titanyl phthalocyanine that absorbs light of a wavelength of from about 370 to about 950 nanometers; an imaging member wherein the supporting substrate is comprised of a conductive substrate comprised of a metal; an imaging member wherein the conductive substrate is aluminum, aluminized polyethylene terephthalate, or titanized polyethylene terephthalate; an imaging member wherein the photogenerating resinous binder is selected from the group consisting of polyesters, polyvinyl butyrals, polycarbonates, polystyrene-b-polyvinyl pyridine, and polyvinyl formals; a photoconductor wherein at least one or each of a plurality of the charge transport layers comprises hole transport molecules, such as the aryl amines illustrated herein, and more specifically, of the structure/formula

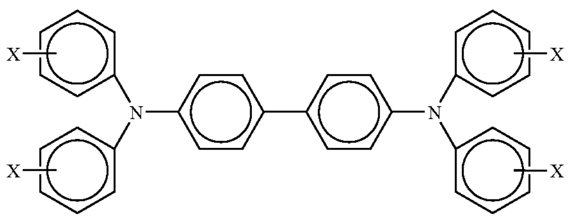

wherein each X substituent, which can be located in the para or meta positions, is selected from the group consisting of at least one of alkyl, alkoxy, substituted alkyl, substituted alkoxy, and halogen; wherein at least one charge transport layer is one, from one to about 5, 1, 2, 3, 4, 5, and the like; an imaging member wherein alkyl and alkoxy contain from about 1 to about 15 carbon atoms; an imaging member wherein for the charge transport aryl amines alkyl contains from about 1 to about 5 carbon atoms; a photoconductor or an imaging member wherein each of or at least one of the charge transport layers comprises

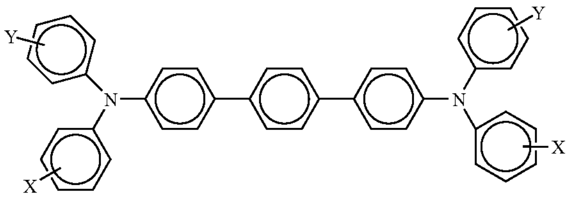

wherein X and Y are independently alkyl, alkoxy, aryl, substituted alkyl, substituted alkoxy, substituted aryl, a halogen such as fluoride, chloride, bromide or iodide, or mixtures thereof; an imaging member wherein alkyl and alkoxy contain from about 1 to about 12 carbon atoms; a photoconductive imaging member wherein for each charge transport layer there is selected in a suitable effective amount an aryl terphenyl amine selected from the group consisting of N,N'-bis(4-butylphenyl)-N,N'-di-p-tolyl-[p-terphenyl]-4,4"-diamine, N,N'-bis(4-butylphenyl)-N,N'-di-m-tolyl-[p-terphenyl]-4, 4"-diamine, N, N'-bis(4-butylphenyl)-N,N'-di-o-tolyl-[p-terphenyl]-4,4"-diamine, N,N'-bis(4-butylphenyl)-N,N'-bis-(4-isopropylphenyl)-[p-terphenyl]-4,4"-diamine, N,N'-bis(4-butylphenyl)-N,N'-bis-(2-ethyl-6-methylphenyl)-[p-terphenyl]-4,4"-diamine, N,N'-bis(4-butylphenyl)-N,N'-bis-(2,5-dimethylphenyl)-[p-terphenyl]-4,4"-diamine, N,N'-diphenyl-N,N'-bis(3-chlorophenyl)-[p-terphenyl]-4,4"-diamine, other known terphenyls, and mixtures thereof; a photoconductive imaging member comprised of a supporting substrate, and thereover a layer comprised of titanyl phthalocyanine Type V photogenerating pigments, and charge transport layers; a member wherein the photogenerating layer is situated between the substrate and the charge transport; a member wherein the charge transport layer is situated between the substrate and the photogenerating layer; a member wherein the photogenerating layer is of a thickness of from about 0.1 to about 45 microns; a member wherein the photogenerating component amount is from about 20 weight percent to about 90 weight percent, and wherein the photogenerating pigment is optionally dispersed in from about 10 weight percent to about 80 weight percent of a polymer binder; a member wherein the thickness of the photogenerating layer is from about 0.2 to about 12 microns; a member wherein the photogenerating and charge transport layer components are contained in a polymer binder; a member wherein the binder is present in an amount of from about 55 to about 95 percent by weight, and wherein the total of the layer components is about 100 percent; an imaging member with a blocking layer contained as a coating on a substrate, and an adhesive layer coated on the blocking layer; an imaging member further containing an adhesive layer and a hole blocking layer; and a color imaging method which comprises generating an electrostatic latent image on the imaging member, developing the latent image, transferring, and fixing the developed electrostatic image to a suitable substrate.

Examples of components or materials optionally incorporated into the charge transport layers or at least one charge transport layer to, for example, enable excellent lateral charge migration (LCM) resistance include hindered phenolic antioxidants such as tetrakis methylene(3,5-di-tert-butyl-4-hydroxy hydrocinnamate) methane (IRGANOX® 1010, available from Ciba Specialty Chemical), butylated hydroxytoluene (BHT), and other hindered phenolic antioxidants including SUMILIZER™ BHT-R, MDP-S, BBM-S, WX-R, NW, BP-76, BP-101, GA-80, GM and GS (available from Sumitomo Chemical Co., Ltd.), IRGANOX® 1035, 1076, 1098, 1135, 1141, 1222, 1330, 1425WL, 1520L, 245, 259, 3114, 3790, 5057 and 565 (available from Ciba Specialties Chemicals), and ADEKA STAB™ AO-20, AO-30, AO-40, AO-50, AO-60, AO-70, AO-80 and AO-330 (available from Asahi Denka Co., Ltd.); hindered amine antioxidants such as SANOL™ LS-2626, LS-765, LS-770 and LS-744 (available from SNKYO CO., Ltd.), TINUVIN® 144 and 622LD (available from Ciba Specialties Chemicals), MARK™ LA57, LA67, LA62, LA68 and LA63 (available from Asahi Denka Co., Ltd.), and SUMILIZER® TPS (available from Sumitomo Chemical Co., Ltd.); thioether antioxidants such as SUMILIZER® TP-D (available from Sumitomo Chemical Co., Ltd); phosphite antioxidants such as MARK™ 2112, PEP-8, PEP-24G, PEP-36, 329K and HP-10 (available from Asahi Denka Co., Ltd.); other molecules such as bis(4-diethylamino-2-methylphenyl)phenylmethane (BDETPM), bis-[2-methyl-4-(N-2-hydroxyethyl-N-ethylaminophenyl)]-phenylmethane (DHTPM), and the like. The weight percent of the antioxidant in at least one of the charge transport layers is from about 0 to about 20, from about 1 to about 10, or from about 3 to about 8 weight percent.

The following Examples are being submitted to illustrate embodiments of the present disclosure. These Examples are intended to be illustrative only and are not intended to limit the scope of the present disclosure. Also, parts and percentages are by weight unless otherwise indicated.

COMPARATIVE SYNTHESIS EXAMPLE 1

Preparation of Type I Titanyl Phthalocyanine:

A Type I titanyl phthalocyanine (TiOPc) was prepared as follows. To a 300 milliliter three-necked flask fitted with mechanical stirrer, condenser, and thermometer maintained under an argon atmosphere were added 3.6 grams (0.025 mole) of 1,3-diiminoisoindoline, 9.6 grams (0.075 mole) of o-phthalonitrile, 75 milliliters (80 weight percent) of tetrahydronaphthalene, and 7.11 grams (0.025 mole) of titanium tetrapropoxide (all obtained from Aldrich Chemical Company, except phthalonitrile which was obtained from BASF). The resulting mixture (20 weight percent of solids) was stirred and warmed to reflux (about 198° C.) for 2 hours. The resultant black suspension was cooled to about 150° C., and then was filtered by suction through a 350 milliliter M-porosity sintered glass funnel, which had been preheated with boiling dimethyl formamide (DMF). The solid Type I TiOPc product resulting was washed with two 150 milliliter portions of boiling DMF, and the filtrate, initially black, became a light blue-green color. The solid was slurried in the funnel with 150 milliliters of boiling DMF, and the suspension was filtered. The resulting solid was washed in the funnel with 150 milliliters of DMF at 25° C., and then with 50 milliliters of methanol. The resultant shiny purple solid was dried at 70° C. overnight, about 18 hours, to yield 10.9 grams (76 percent) of pigment, which was identified as Type I TiOPc on the basis of its X-ray powder diffraction trace. Elemental analysis of the product indicated C, 66.54; H, 2.60; N, 20.31; and Ash ($TiO_2$), 13.76. TiOPc requires (theory): C, 66.67; H, 2.80; N, 19.44; and Ash, 13.86.

A Type I titanyl phthalocyanine can also be prepared in 1-chloronaphthalene or N-methyl pyrrolidone as follows. A 250 milliliter three-necked flask fitted with mechanical stirrer, condenser, and thermometer maintained under an atmosphere of argon was charged with 1,3-diiminoisoindolene (14.5 grams), titanium tetrabutoxide (8.5 grams), and 75 milliliters of 1-chloronaphthalene (ClNp) or N-methyl pyrrolidone. The mixture was stirred and warmed. At 140° C. the mixture turned dark green and began to reflux. At this time the vapor (which was identified as n-butanol by gas chromatography) was allowed to escape into the atmosphere until the reflux temperature reached 200° C. The reaction was maintained at this temperature for two hours then was cooled to 150° C. The product was filtered through a 150 milliliter M-porosity sintered glass funnel, which was preheated to approximately 150° C. with boiling DMF, and then washed thoroughly with three portions of 150 milliliters of boiling DMF, followed by washing with three portions of 150 milliliters of DMF at room temperature, and then three portions of 50 milliliters of methanol, thus providing 10.3 grams (72 percent yield) of a shiny purple pigment, which was identified as Type I TiOPc by X-ray powder diffraction (XRPD).

Preparation of Type V Titanyl Phthalocyanine:

Fifty grams of TiOPc Type I, prepared above, were dissolved in 300 milliliters of a trifluoroacetic acid (pKa of −0.25)/methylene chloride (1/4, volume/volume) mixture for 1 hour in a 500 milliliter Erlenmeyer flask with a magnetic stirrer. At the same time, 2,600 milliliters of methanol/methylene chloride (1/1, volume/volume) quenching mixture were cooled with a dry ice bath for 1 hour in a 3,000 milliliter beaker with a magnetic stirrer, and the final temperature of the mixture was about −25° C. The resulting TiOPc solution was transferred to a 500 milliliter addition funnel with a pressure-equalization arm, and added into the cold quenching mixture over a period of 30 minutes. The mixture obtained was then allowed to stir for an additional 30 minutes, and subsequently hose-vacuum filtered through a 2,000 milliliter Buchner funnel with a fibrous glass frit of from about 4 to about 8 μm in porosity. The pigment resulting was then well mixed with 1,500 milliliters of methanol in the funnel, and vacuum filtered. The pigment was then well mixed with 1,000 milliliters of hot water (>90° C.), and vacuum filtered in the funnel four times. The pigment was then well mixed with 1,500 milliliters of cold water, and vacuum filtered in the funnel. The final water filtrate was measured for conductivity, which was below about 10 μS. The resulting wet cake contained approximately 50 weight percent of water. A small portion of the wet cake was dried at 65° C. under vacuum and a blue pigment was obtained. A representative XRPD of this pigment after quenching with methanol/methylene chloride was identified by XRPD as Type Y titanyl phthalocyanine.

The remaining portion of the wet cake was redispersed in 700 grams of monochlorobenzene (MCB) in a 1,000 milliliter bottle, and roll mixed for one hour. The dispersion was vacuum filtered through a 2,000 milliliter Buchner funnel with a fibrous glass frit of 4 to 8 μm in porosity over a period of two hours. The pigment was then well mixed with 1,500 milliliters of methanol, and filtered in the funnel twice. The final pigment was vacuum dried at 60° C. to 65° C. for two days. Approximately 45 grams of the pigment were obtained. The XRPD of the resulting pigment after the MCB conversion was designated as a Type V titanyl phthalocyanine. The Type V had an X-ray diffraction pattern having characteristic diffraction peaks at a Bragg angle of $2\Theta\pm0.2°$ at about 9.0°, 9.6°, 24.0°, and 27.2°.

SYNTHESIS EXAMPLE I

Preparation of Type I Titanyl Phthalocyanine:

A Type I titanyl phthalocyanine (TiOPc) was prepared as follows. To a 300 milliliter three-necked flask fitted with mechanical stirrer, condenser and thermometer maintained under an argon atmosphere were added 3.6 grams (0.025 mole) of 1,3-diiminoisoindoline, 9.6 grams (0.075 mole) of o-phthalonitrile, 75 milliliters (80 weight percent) of tetrahydronaphthalene and 7.11 grams (0.025 mole) of titanium tetrapropoxide (all obtained from Aldrich Chemical Company, except phthalonitrile which was obtained from BASF). The resulting mixture (20 weight percent of solids) was stirred and warmed to reflux (about 198° C.) for 2 hours. The resultant black suspension was cooled to about 150° C., and then was filtered by suction through a 350 milliliter M-porosity sintered glass funnel, which had been preheated with boiling dimethyl formamide (DMF). The solid Type I TiOPc product resulting was washed with two 150 milliliter portions of boiling DMF, and the filtrate, initially black, became a light blue-green color. The solid was slurried in the funnel with 150 milliliters of boiling DMF and the suspension was filtered. The resulting solid was washed in the funnel with 150 milliliters of DMF at 25° C., and then with 50 milliliters of methanol. The resultant shiny purple solid was dried at 70° C. overnight, about 18 hours, to yield 10.9 grams (76 percent) of pigment, which was identified as Type I TiOPc on the basis of its X-ray powder diffraction trace. Elemental analysis of the product indicated C, 66.54; H, 2.60; N, 20.31; and Ash ($TiO_2$), 13.76. TiOPc requires (theory): C, 66.67; H, 2.80; N, 19.44; and Ash, 13.86.

A Type I titanyl phthalocyanine can also be prepared in 1-chloronaphthalene or N-methyl pyrrolidone as follows. A 250 milliliter three-necked flask fitted with mechanical stirrer, condenser, and thermometer maintained under an atmosphere of argon was charged with 1,3-diiminoisoindolene (14.5 grams), titanium tetrabutoxide (8.5 grams), and 75 milliliters of 1-chloronaphthalene (ClNp) or N-methyl pyrrolidone. The mixture was stirred and warmed. At 140° C. the mixture turned dark green and began to reflux. At this time the vapor (which was identified as n-butanol by gas chromatography) was allowed to escape to the atmosphere until the reflux temperature reached 200° C. The reaction was maintained at this temperature for two hours, then was cooled to 150° C. The product was filtered through a 150 milliliter M-porosity sintered glass funnel, which was preheated to approximately 150° C. with boiling DMF, and then washed thoroughly with three portions of 150 milliliters of boiling DMF, followed by washing with three portions of 150 milliliters of DMF at room temperature, and then three portions of 50 milliliters of methanol, thus providing 10.3 grams (72 percent yield) of a shiny purple pigment, which was identified as Type I TiOPc by X-ray powder diffraction (XRPD).

Treatment of Type I Titanyl Phthalocyanine with Weak Acid:

Twenty grams of the above prepared Type I titanyl phthalocyanine were mixed with a mixture of water and glacial acetic acid with a pKa of 4.76 (20/1, v/v) for half an hour, and the mixture was subsequently hose-vacuum filtered through a 600 milliliter Buchner funnel with a fibrous glass frit of from about 4 to about 8 μm in porosity. The pigment resulting was then well mixed with 800 milliliters of hot water (>90° C.), and vacuum filtered in the funnel. The pigment was then mixed with 800 milliliters of cold water, thoroughly mixed, and vacuum filtered in the funnel. The final water filtrate was measured for conductivity, which was below about 10 μS. The resulting wet cake was then thoroughly mixed with 800 milliliters of methanol, and vacuum filtered in the funnel. The wet cake was dried at 65° C. under vacuum, and the product obtained was identified as Type I TiOPc on the basis of its X-ray powder diffraction trace.

Preparation of Type V Titanyl Phthalocyanine:

Fifty grams of the weak acid treated TiOPc Type I, prepared above, were dissolved in 300 milliliters of a trifluoroacetic acid (pKa of −0.25)/methylene chloride (1/4, volume/volume) mixture for 1 hour in a 500 milliliter Erlenmeyer flask with a magnetic stirrer. At the same time, 2,600 milliliters of methanol/methylene chloride (1/1, volume/volume) quenching mixture were cooled with a dry ice bath for 1 hour in a 3,000 milliliter beaker with a magnetic stirrer, and the final temperature of the mixture was about −25° C. The resulting TiOPc solution was transferred to a 500 milliliter addition funnel with a pressure-equalization arm, and added into the cold quenching mixture over a period of 30 minutes. The mixture obtained was then allowed to stir for an additional 30 minutes, and subsequently hose-vacuum filtered through a 2,000 milliliter Buchner funnel with a fibrous glass frit of from about 4 to about 8 μm in porosity. The pigment resulting was then well mixed with 1,500 milliliters of methanol in the funnel, and vacuum filtered. The pigment was then well mixed with 1,000 milliliters of hot water (>90° C.), and vacuum filtered in the funnel four times. The pigment was then well mixed with 1,500 milliliters of cold water, and vacuum filtered in the funnel. The final water filtrate was measured for conductivity, which was below about 10 μS. The resulting wet cake contained approximately 50 weight percent of water. A small portion of the wet cake was dried at 65° C. under vacuum, and a blue pigment was obtained. A representative XRPD of this pigment after quenching with methanol/methylene chloride was identified by XRPD as Type Y titanyl phthalocyanine.

The remaining portion of the wet cake was redispersed in 700 grams of monochlorobenzene (MCB) in a 1,000 milliliter bottle and rolled for an hour. The dispersion was vacuum filtered through a 2,000 milliliter Buchner funnel with a fibrous glass frit of 4 to 8 μm in porosity over a period of two hours. The pigment was then well mixed with 1,500 milliliters of methanol and filtered in the funnel twice. The final pigment was vacuum dried at 60° C. to 65° C. for two days. Approximately 45 grams of the pigment were obtained. The XRPD of the resulting pigment after the MCB conversion was designated as a Type V titanyl phthalocyanine. The Type V had an X-ray diffraction pattern having characteristic diffraction peaks at a Bragg angle of $2\Theta \pm 0.2°$ at about 9.0°, 9.6°, 24.0°, and 27.2°.

COMPARATIVE EXAMPLE 1

A photoconductor was prepared by providing a 0.02 micrometer thick titanium layer coated on a biaxially oriented polyethylene naphthalate substrate (KALEDEX™ 2000) having a thickness of 3.5 mils, and applying thereon, with a gravure applicator or an extrusion coater, a solution containing 50 grams of 3-amino-propyltriethoxysilane, 41.2 grams of water, 15 grams of acetic acid, 684.8 grams of denatured alcohol, and 200 grams of heptane. This layer was then dried for about 5 minutes at 135° C. in the forced air dryer of the coater. The resulting blocking layer had a dry thickness of 500 Angstroms. An adhesive layer was then prepared by applying a wet coating over the blocking layer, using a gravure applicator or an extrusion coater, and which adhesive contained 0.2 percent by weight, based on the total weight of the solution, of the copolyester adhesive (ARDEL™ D100 available from Toyota Hsutsu Inc.) in a 60:30:10 volume ratio mixture of tetrahydrofuran/monochlorobenzene/methylene chloride. The adhesive layer was then dried for about 5 minutes at 135° C. in the forced air dryer of the coater. The resulting adhesive layer had a dry thickness of 200 Angstroms.

A photogenerating layer dispersion was prepared by introducing 0.45 gram of the known polycarbonate IUPILON 200™ (PCZ-200) or Polycarbonate Z, weight average molecular weight of 20,000, available from Mitsubishi Gas Chemical Corporation, and 50 milliliters of monochlorobenzene into a 4 ounce glass bottle. To this solution were added 2.4 grams of titanyl phthalocyanine (TiOPc, Type V) of Comparative Synthesis Example 1 and 300 grams of ⅛ inch (3.2 millimeters) diameter stainless steel shot. This mixture was then placed on a ball mill for 8 hours. Subsequently, 2.25 grams of PCZ-200 were dissolved in 46.1 grams of monochlorobenzene, and added to the titanyl phthalocyanine dispersion. This slurry was then placed on a shaker for 10 minutes. The resulting dispersion was, thereafter, applied to the above adhesive interface with a Bird applicator to form a photogenerating layer having a wet thickness of 0.50 mil. A strip about 10 millimeters wide along one edge of the substrate web bearing the blocking layer and the adhesive layer was deliberately left uncoated by any of the photogenerating layer material to facilitate adequate electrical contact by the ground strip layer that was applied later. The photogenerating layer was dried at 120° C. for 1 minute in a forced air oven to form a dry photogenerating layer having a thickness of 0.8 micron.

The imaging member or photoconductor web was then overcoated with a two-layer charge transport layer. Specifically, the photogenerating layer was overcoated with a charge transport layer (the bottom layer) in contact with the photogenerating layer. The bottom layer of the charge transport layer was prepared by introducing into an amber glass bottle in a weight ratio of 1:1 N,N'-diphenyl-N,N'-bis(3-methylphenyl)-1,1'-biphenyl-4,4'-diamine and MAKROLON® 5705, a known polycarbonate resin having a molecular weight average of from about 50,000 to about 100,000, commercially available from Farbenfabriken Bayer A.G. The resulting mixture was then dissolved in methylene chloride to form a solution containing 15 percent by weight solids. This solution was applied on the photogenerating layer to form a coating of the bottom layer that upon drying (120° C. for 1 minute) had a thickness of 14.5 microns. During this coating process, the humidity was equal to or less than 15 percent.

The bottom layer of the charge transport layer was overcoated with a top layer. The charge transport layer solution of the top layer was prepared as described above for the bottom layer. This solution was applied on the bottom layer of the charge transport layer to form a coating that upon drying (120° C. for 1 minute) had a thickness of 14.5 microns. During this coating process, the humidity was equal to or less than 15 percent.

EXAMPLE II

A photoconductor was prepared by repeating the process of Comparative Example 1 except that the titanyl phthalocyanine used was prepared and illustrated in Synthesis Example I.

Electrical Property Testing

The above prepared photoconductor devices (Comparative Example 1 and Example I) were tested in a scanner set to obtain photoinduced discharge cycles, sequenced at one charge-erase cycle followed by one charge-expose-erase cycle wherein the light intensity was incrementally increased with cycling to produce a series of photoinduced discharge characteristic curves from which the photosensitivity and surface potentials at various exposure intensities were measured. Additional electrical characteristics were obtained by a series of charge-erase cycles with incrementing surface potential to generate several voltage versus charge density curves. The scanner was equipped with a scorotron set to a constant voltage charging at various surface potentials. The devices were tested at surface potentials of 500 volts with the exposure light intensity incrementally increased by means of regulating a series of neutral density filters; the exposure light source is a 780 nanometer light emitting diode. The xerographic simulation was completed in an environmentally controlled light tight chamber at ambient conditions (40 percent relative humidity and 22° C.).

There was essentially no difference in PIDC between these two devices. Treatment of the Type I titanyl phthalocyanine with a weak acid did not change the electrical responses of the photoconductor device.

Charge Deficient Sposts (CDS) Measurements

Various known methods have been developed to assess and/or accommodate the occurrence of charge deficient spots. For example, U.S. Pat. Nos. 5,703,487 and 6,008,653, the disclosures of each patent being totally incorporated herein by reference, disclose processes for ascertaining the microdefect levels of an electrophotographic imaging member or photoconductor. The method of U.S. Pat. No. 5,703,487, the disclosure of which is totally incorporated herein by reference, designated as field-induced dark decay (FIDD), involves measuring either the differential increase in charge over and above the capacitive value or measuring reduction in voltage below the capacitive value of a known imaging member and of a virgin imaging member, and comparing differential increase in charge over and above the capacitive value or the reduction in voltage below the capacitive value of the known imaging member and of the virgin imaging member.

U.S. Pat. Nos. 6,008,653 and 6,150,824, the disclosures of each patent being totally incorporated herein by reference, disclose a method for detecting surface potential charge patterns in an electrophotographic imaging member with a floating probe scanner. Floating Probe Micro Defect Scanner (FPS) is a contactless process for detecting surface potential charge patterns in an electrophotographic imaging member. The scanner includes a capacitive probe having an outer shield electrode, which maintains the probe adjacent to and spaced from the imaging surface to form a parallel plate capacitor with a gas between the probe and the imaging surface, a probe amplifier optically coupled to the probe, establishing relative movement between the probe and the imaging surface, a floating fixture which maintains a substantially constant distance between the probe and the imaging surface. A constant voltage charge is applied to the imaging surface prior to relative movement of the probe and the imaging surface past each other, and the probe is synchronously biased to within about +/−300 volts of the average surface potential of the imaging surface to prevent breakdown, measuring variations in surface potential with the probe, compensating the surface potential variations for variations in distance between the probe and the imaging surface, and comparing the compensated voltage values to a baseline voltage value to detect charge patterns in the electrophotographic imaging member. This process may be conducted with a contactless scanning system comprising a high resolution capacitive probe, a low spatial resolution electrostatic voltmeter coupled to a bias voltage amplifier, and an imaging member having an imaging surface capacitively coupled to and spaced from the probe and the voltmeter. The probe comprises an inner electrode surrounded by and insulated from a coaxial outer Faraday shield electrode, the inner electrode connected to an opto-coupled amplifier, and the Faraday shield connected to the bias voltage amplifier. A threshold of 20 volts is commonly chosen to count charge deficient spots.

The above prepared photoconductors were measured for CDS counts using the above-described FPS technique, and the results follow in Table 1.

TABLE 1

| | CDS (Counts/$cm^2$) |
|---|---|
| Comparative Example 1 | 41 |
| Example I | 8 |

The above data demonstrates that the CDS for the photoconductor of Example I where the Type I titanyl phthalocyanine was treated with a weak acid prior to the acid pasting, and the conversion exhibited a significantly lower CDS than the photoconductor of Comparative Example 1 where the Type I titanyl phthalocyanine was not treated with a weak acid prior to the acid pasting and the conversion. More specifically, the CDS was about one fifth of the controlled Comparative Example 1.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

What is claimed is:

1. A process for preparing a high sensitivity titanyl phathocyanine, which comprises treating a Type I titanyl phthalocyanine with a weak acid having a pKa of at least equal to or greater than about −0.25; dissolving the weak acid treated Type I titanyl phthalocyanine in a solution comprising a trihaloacetic acid and an alkylene halide; adding said mixture comprising the dissolved Type I titanyl phthalocyanine to a solution comprising an alcohol and an alkylene halide thereby precipitating a Type Y titanyl phthalocyanine; and treating said Type Y titanyl phthalocyanine with monohalobenzene thereby resulting in a high sensitivity titanyl phthalocyanine.

2. A process in accordance with claim 1 wherein said pKa is from about 0 to about 15, and wherein said weak acid captures the metallic impurities present in said titanyl phthalocyanine Type I.

3. A process in accordance with claim 1 wherein said pKa is from about 1 to about 10, and wherein the titanyl phthalocyanine obtained is Type V titanyl phthalocyanine.

4. A process in accordance with claim 1 wherein said pKa is from about 2 to about 6 wherein the titanyl phthalocyanine obtained is Type V titanyl phthalocyanine.

5. A process in accordance with claim 1 wherein said acid is selected from the group consisting of acetic acid, phosphoric acid, hydrofluoric acid, monofluoroacetic acid, monochloroacetic acid, monobromoacetic acid, monoiodoacetic acid, dichloroacetic acid, trichloroacetic acid, formic acid, oxalic acid, acetylsalicylic acid, nicotinic acid, pyruvic acid, propionic acid, oxalacetic acid, and mixtures thereof.

6. A process in accordance with claim 1 wherein said acid is an acidic aqueous solution containing from about 1 weight percent to about 50 weight percent of the acid.

7. A process in accordance with claim 1 wherein said acid is an acidic aqueous solution containing from about 2 weight percent to about 20 weight percent of the acid.

8. A process in accordance with claim 1 wherein the ratio of said titanyl phthalocyanine Type I to said acid is from about 90/10 to about 30/70.

9. A process in accordance with claim 1 wherein the ratio of said titanyl phthalocyanine Type I to said acid is from about 80/20 to about 40/60.

10. A process in accordance with claim 1 wherein the ratio of said titanyl phthalocyanine Type I to said acid is from about 70/30 to about 50/50 wherein the titanyl phthalocyanine obtained is Type V titanyl phthalocyanine, and wherein there is removed from said titanyl phthalocyanine Type I metallic impurities prior to its acid pasting thereof, and conversion to titanyl phthalocyanine Type V.

11. A process in accordance with claim 1 wherein said titanyl phthalocyanine Type I is subjected to filtration, isolation, and drying, and wherein there is removed from said titanyl phthalocyanine Type I metallic impurities prior to its acid pasting and conversion to titanyl phthalocyanine Type V.

12. A process in accordance with claim 1 wherein said titanyl phthalocyanine Type Y is subjected to mixing with said monohalobenzene, followed by filtration, isolation, and drying.

13. A process in accordance with claim 1 wherein there results titanyl phthalocyanine Type V with an X-ray diffraction pattern having characteristic diffraction peaks at a Bragg angle $2\Theta \pm 0.2°$ at about 9°, 9.6°, 24°, and 27.2°.

14. A process in accordance with claim 1 wherein said solution comprising an alcohol and an alkylene halide has an alcohol to alkylene halide ratio of from about 1/4 (v/v) to about 4/1 (v/v), and said titanyl phthalocyanine is Type V titanyl phthalocyanine, and wherein the resulting Type V titanyl phthalocyanine has an X-ray diffraction pattern having characteristic diffraction peaks at a Bragg angle $2\Theta \pm 0.2°$ at about 9°, 9.6°, 24°, and 27.2°, and wherein said solution comprising an alcohol and an alkylene halide comprises methanol and methylene chloride.

15. A process in accordance with claim 1 wherein said monohalobenzene is monochlorobenzene.

16. A process in accordance with claim 1 wherein said titanyl phthalocyanine is prepared by treating said Type I titanyl phthalocyanine with a weak acid aqueous solution; dissolving the acid treated Type I titanyl phthalocyanine in a solution of trifluoroacetic acid and methylene chloride; precipitating a Type Y titanyl phthalocyanine by adding said solution of trifluoroacetic acid, methylene chloride, and the Type I titanyl phthalocyanine to a solution of methanol and methylene chloride; washing said Type Y titanyl phthalocyanine; and converting the Type Y titanyl phthalocyanine to a Type V titanyl phthalocyanine by treating said Type Y titanyl phthalocyanine with monochlorobenzene.

17. A process in accordance with claim 1 wherein said acid is acetic acid; said monohalobenzene is chlorobenzene; said alkylene halide is alkylene chloride; and said acid is glacial acetic acid.

* * * * *